(12) United States Patent
Rath et al.

(10) Patent No.: US 11,547,693 B2
(45) Date of Patent: *Jan. 10, 2023

(54) ASCORBATE IN THE PREVENTION OF STATIN INDUCED VASCULAR CALCIFICATION

(71) Applicants: Matthias Rath, Aptos, CA (US);
Vadim Ivanov, San Jose, CA (US);
Aleksandra Niedzwiecki, Aptos, CA (US)

(72) Inventors: Matthias Rath, Aptos, CA (US);
Vadim Ivanov, San Jose, CA (US);
Aleksandra Niedzwiecki, Aptos, CA (US)

(73) Assignees: Matthias Rath, Aptos, CA (US);
Vadim Ivanov, San Jose, CA (US);
Aleksandra Niedzwiecki, Aptos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/524,383

(22) Filed: Jul. 29, 2019

(65) Prior Publication Data

US 2021/0030715 A1 Feb. 4, 2021

(51) Int. Cl.
*A61K 31/375* (2006.01)
*A61K 31/455* (2006.01)
(Continued)

(52) U.S. Cl.
CPC .......... *A61K 31/375* (2013.01); *A61K 31/122* (2013.01); *A61K 31/235* (2013.01);
(Continued)

(58) Field of Classification Search
CPC .. A61K 31/375; A61K 31/122; A61K 31/235; A61K 31/366; A61K 31/40;
(Continued)

(56) References Cited

U.S. PATENT DOCUMENTS

| 4,929,437 A | 5/1990 | Tobert |
| 2004/0009986 A1 | 1/2004 | Ohsawa |

(Continued)

FOREIGN PATENT DOCUMENTS

| EP | 1214893 A1 | 6/2002 | |
| WO | 03/072013 A2 | 9/2003 | |
| WO | WO-2017062954 A1 * | 4/2017 | ............. A61K 45/06 |

OTHER PUBLICATIONS

Cleveland Clinic, "Cardiovascular Disease: Prevention & Reversal", Dec. 20, 2018, download from https://my.clevelandclinic.org/health/articles/17385-cardiovascular-disease-prevention--reversal on Aug. 6, 2021. (Year: 2018).*

(Continued)

*Primary Examiner* — Jianfeng Song
(74) *Attorney, Agent, or Firm* — Raphael Bellum PLLC

(57) ABSTRACT

A method of treating or preventing vascular calcification in a patient by administering L-ascorbic acid or ascorbate to the patient and a pharmaceutical composition containing at least one statin and L-ascorbic acid or ascorbate in a dosage form that allows for the concomitant administering of the at least one statin and L-ascorbic acid or ascorbate to a patient.

13 Claims, 3 Drawing Sheets

(51) Int. Cl.
| | |
|---|---|
| *A61K 31/40* | (2006.01) |
| *A61K 31/44* | (2006.01) |
| *A61K 31/404* | (2006.01) |
| *A61K 31/366* | (2006.01) |
| *A61K 31/235* | (2006.01) |
| *A61K 31/505* | (2006.01) |
| *A61K 31/122* | (2006.01) |
| *A61P 3/14* | (2006.01) |

(52) U.S. Cl.
CPC ............ *A61K 31/366* (2013.01); *A61K 31/40* (2013.01); *A61K 31/404* (2013.01); *A61K 31/44* (2013.01); *A61K 31/455* (2013.01); *A61K 31/505* (2013.01); *A61P 3/14* (2018.01)

(58) Field of Classification Search
CPC .... A61K 31/404; A61K 31/44; A61K 31/455; A61K 31/505; A61P 3/14
See application file for complete search history.

(56) References Cited

U.S. PATENT DOCUMENTS

| | | | |
|---|---|---|---|
| 2004/0014712 A1 | 1/2004 | Ohsawa | |
| 2004/0023919 A1 | 2/2004 | Ohsawa | |
| 2006/0223838 A1* | 10/2006 | Jiang | A61P 9/00 514/284 |
| 2009/0074883 A1 | 3/2009 | Gupta | |
| 2010/0021573 A1 | 1/2010 | Gonzalez et al. | |
| 2010/0061968 A1* | 3/2010 | Lines | A61K 31/375 424/93.51 |
| 2010/0178341 A1 | 7/2010 | Issa et al. | |
| 2011/0104137 A1 | 5/2011 | Richardson et al. | |
| 2013/0115281 A1 | 5/2013 | Draper et al. | |
| 2015/0056274 A1* | 2/2015 | Zemel | A23L 33/15 424/451 |
| 2017/0000780 A1* | 1/2017 | Zemel | A61K 31/455 |

OTHER PUBLICATIONS

Ikegami et al., "The annual rate of coronary artery calcification with combination therapy with a PCSK9 inhibitor and a statin is lower than that with statin monotherapy", NPJ Aging Mechanisms of Disease, Jan. 27, 2018; pp. 1-8.

Puri et al., "Impact of Statins on Serial Coronary Calcification During Atheroma Progression and Regression", Journal of the American College of Cardiology, vol. 65, No. 13, Apr. 7, 2015 pp. 1273-1282.

Kadohira et al., "Impact of chronic statin therapy on clinical presentation and underlying lesion morphology in patients undergoing percutaneous intervention: an ADAPT-DES IVUS substudy", Coronary Artery Disease, 2017; 28; pp. 218-224.

Ivanov et al., "Extracellular Matrix-Mediated Control of Aortic Smooth Muscle Cell Growth and Migration by a Combination of Ascorbic Acid, Lysine, Praline, and Catechins", J. Cardiovasc Pharmacol Nov. 2007; vol. 50 No. 5, pp. 541-547.

Cha et al., "Hypoascorbemia induces atherosclerosis and vascular deposition of lipoprotein(a) in transgenic mice", Am. J. Cardiovasc Dis, 2015; vol. 5, No. 1, pp. 53-62.

Rath et al., "Nutritional Supplement Program Halts Progression of Early Coronary Atherosclerosis Documented by Ultrafast Computed Tomography", Journal of Applied Nutrition, vol. 48, No. 3, 1996, pp. 67-78.

Ivanov et al., "Plant-Derived Micronutrients Suppress Monocyte Adhesion to Cultured Human Aortic Endothelial Cell Layer by Modulating Its Extracellular Matrix Composition", J. Cardiovasc Pharmacol, Jul. 2008; vol. 52, No. 1, pp. 55-65.

Arad et al, "Treatment of Asymptomatic Adults With Elevated Coronary Calcium Scores With Atorvastatin, Vitamin C, and Vitamin E" The St. Francis Heart Study Randomized Clinical Trial, Journal of the American College of Cardiology, vol. 46, No. 1, 2005, pp. 166-172.

Trion et al, "Modulation of calcification of vascular smooth muscle cells in culture by calcium antagonists, statins, and their combination", Molecular and Cellular Biochemistry, vol. 308, No. 1-2, 2007, pp. 25-33.

Skafi et al, "Phospholipase D: A new mediator during high phosphate-induced vascular calcification associated with chronic kidney disease", Journal of Cellular Physiology, vol. 234, No. 4, 2018, pp. 4825-4839.

Panh et al, "Coronary artery calcification: From crystal to plaque rupture", Archives of Cardiovascular Disease, vol. 110, No. 10, 2017, pp. 550-561.

Samadikhah—"Efficacy of Combination Therapy of Statin and Vitamin C in Comparison with Statin in the Prevention of Post-CABG Atrial Fibrillation", (Advanced Pharmaceutical Bulletin, 2014, 4(1), 97-100).

International Search Report from International Application No. PCT/IB2020/057063, dated Feb. 22, 2021.

McCullough, "Effects of Lipid Modification on Progression of Coronary Calcification", J Am Soc Nephrol 16: S115-S119, 2005. (Year: 2005).

Ikegami et al., "The annual rate of coronary artery calcification with combination therapy with a PCSK9 inhibitor and a statin is lower than that with statin monotherapy", npj, Jun. 22, 2018, pp. 1-8.

Saremi et al., Diabetes Care 2012, 35:2390-2392.

Xian et al., Arterioscler. Thromb. Vasc. Biol. 2021, 41:e185-e192.

* cited by examiner

ASCORBATE IN THE PREVENTION OF STATIN INDUCED VASCULAR CALCIFICATION

TECHNICAL FIELD

The present invention relates to the use of L-ascorbic acid or ascorbate for preventing or mitigating the vascular calcification induced by statins.

BACKGROUND

Statins are also known as HMG-CoA reductase inhibitors and are a class of lipid-lowering compounds.

Low-density lipoprotein (LDL) carriers of cholesterol play an important role in the development of atherosclerosis and coronary heart disease via the mechanisms described by the lipid hypothesis. Statins are effective in lowering the LDL cholesterol and so are widely used for primary prevention in people having a high risk of cardiovascular disease, as well as in secondary prevention for those who have developed cardiovascular disease.

Upon treatment with statins, patients exhibit side effects including muscle pain, increased risk of diabetes mellitus, and abnormal blood levels of liver enzymes.

In some patients, for example lovastatin leads to myopathy and asymptomatic, but marked and persistent increases in liver transaminases. The transaminase increase produced by lovastatin and other HMG-CoA reductase inhibitors is a direct consequence of the inhibition of the mevalonate synthesis. To counteract the increased transaminase levels observed in a small number of patients, U.S. Pat. No. 4,929,437 teaches the adjunct administration of an effective amount of HMG-CoA reductase inhibitor and an effective amount of coenzyme Q10 in order to counter-act HMG-CoA reductase inhibitor-associated liver damage.

It has furthermore been known that statins increase vascular calcifications, which are a recognized risk factor for heart disease (Ikegami Y, Inoue I, Inoue K, Shinoda Y3, Iida S1, Goto S4, Nakano T5, Shimada A1, Noda M1. The annual rate of coronary artery calcification with combination therapy with a PCSK9 inhibitor and a statin is lower than that with statin monotherapy. NPJ Aging Mech Dis 2018; 4:7).

In the recent analysis of 8 prospective randomized trials using serial coronary intravascular ultrasound, Puri et al. (Puri R, Nicholls S J, Shao M, Kataoka Y, Uno K, Kapadia S R, Tuzcu E M, Nissen S E. Impact of statins on serial coronary calcification during atheroma progression and regression. J Am Coll Cardiol 2015; 65:1273-1282) concluded that independent of their plaque-regressive effects, statins promote coronary atheroma calcification.

Still there is a controversy between arterial calcification being a well-established marker and prognoses index for cardiovascular disease development, statins stimulating effects on arterial calcification and apparent beneficial effects of statin supplementation on clinical events in CVD patients. Some researchers are providing a tending plausible explanation of these conflicting evidences to be a "special" mechanism of arterial calcification under statin treatments which results in greater lesion stability defined as fewer VH-thin-cap fibroatheromas and plaque ruptures and more calcified thick-cap fibroatheromas (Kadohira T1, Mintz G S, Souza C F, Witzenbichler B, Metzger D C, Rinaldi M J, Mazzaferri E L Jr, Duffy P L, Weisz G, Stuckey T D, Brodie B R, Crowley A, Kirtane A J Stone G W, Maehara A. Impact of chronic statin therapy on clinical presentation and underlying lesion morphology in patients undergoing percutaneous intervention: an ADAPT-DES IVUS substudy. Coron Artery Dis 2017; 28:218-224).

Vascular calcification is a relevant pathophysiological process that is associated with coronary atherosclerosis, and is a prognostic marker of cardiovascular morbidity and mortality.

Vascular smooth muscle cells (SMC) have an extraordinary capacity to undergo osteoblastic phenotypical differentiation. Calcification of the intimal and/or medial vascular cell layer leads to differentiation of osteoblasts whether from a smooth muscle cell, a mesenchymal cell, or vascular pericyte, characterized, among others, by increased alkaline phosphatase activity, osteocalcin production and bone matrix secretion. Biochemical mechanisms associated with the conversion of SMC into osteoblastic cells have been elaborated, however the decisive mechanisms of what triggers and/or regulates this process have remained largely elusive.

Recent studies showed that plaque calcification is a dynamic process and related to the degree of vascular inflammation. Several inflammatory factors produced during the different phases of atherosclerosis can induce the expression and activation of osteoblastic cells located within the arterial wall, which, in turn, promote deposition of calcium.

The presence of regulatory proteins along with dedifferentiated osteoblast-like cells was demonstrated to originate from vascular smooth muscle cells (VSMCs) that were designated calcifying vascular cells. These cells are implicated in the synthesis/reabsorption of bone in atherosclerotic plaques, especially around calcification. Thus, it has been proposed that bone cell function in the vascular wall is, in some aspects, similar to that in bones. However, in vitro studies provided evidence that regulation of bone synthesis in the vascular wall and in the skeleton are different. When stimulated by oxidative stress or with oxidized LDL, osteoblasts of the skeleton and CVCs (a population of vascular cells with osteoblastic characteristics) showed opposing response, a decrease and increase of bone formation, respectively.

BRIEF SUMMARY OF THE INVENTION

The object underlying the present invention is to treat or prevent the vascular calcification induced in patients by administration of statins.

The object is achieved according to the present invention by one or more of the following embodiments.

First set of embodiments:
1. L-ascorbic acid or ascorbate for use in concomitantly treating patients receiving statin treatment.
2. L-ascorbic acid or ascorbate for use in treating or preventing vascular calcification in patients.
3. L-ascorbic acid or ascorbate according to embodiment 2 for use in treating or preventing the vascular calcification induced in patients by administration of statins.
4. The use of L-ascorbic acid or ascorbate for mitigating the vascular calcification induced by statins.
5. A pharmaceutical composition containing at least one statin and L-ascorbic acid or ascorbate in a dosage form that allows for the concomitant administering of the at least one statin and L-ascorbic acid or ascorbate to a patient.
6. The pharmaceutical composition according to embodiment 5, wherein the at least one statin and L-ascorbic acid or ascorbate are present as a physical mixture or as separate pharmaceutical compositions intended for concomitant administration to a patient.
7. The pharmaceutical composition according to embodiment 6 for the prevention or treatment of cardiovascular disease.
8. The pharmaceutical composition according to one of embodiments 5 to 7, wherein the cardiovascular disease is coronary artery disease, cerebrovascular disease or peripheral vascular disease.
9. The pharmaceutical composition according to one of embodiments 5 to 8, wherein the statin is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin.
10. The pharmaceutical composition according to one of embodiments 6 to 9, wherein the ascorbate is selected from water-soluble or lipid-soluble ascorbates or mixtures thereof, preferably from calcium ascorbate, magnesium ascorbate, sodium ascorbate, ascorbyl phosphate, ascorbyl palmitate or mixtures thereof.
11. The pharmaceutical composition according to one of embodiments 6 to 10, additionally containing coenzyme $Q_{10}$ in a dosage form that allows for the concomitant administering of the at least one statin, L-ascorbic acid or ascorbate, and coenzyme $Q_{10}$ to a patient.
12. The pharmaceutical composition according to one of embodiments 5 to 11, comprising a daily dosage amount of L-ascorbic acid or ascorbate from 10 mg to 100 g, preferably 100 mg to 10 g, and the lowest to the highest commercially available or clinically applicable dose of at least one statin, preferably from 5 mg to 100 mg.
13. The pharmaceutical composition according to one of embodiments 5 to 12, further comprising one or more additional micronutrients beside L-ascorbic acid or ascorbate, preferably selected from trace minerals, vitamins, and mixtures thereof.
14. The pharmaceutical composition according to embodiment 13, wherein the one or more additional micronutrients contain niacin, preferably in a mixture with the statin.

Second set of embodiments:
1. A method of treating or preventing vascular calcification in a patient, who preferably is treated with statins, by administering L-ascorbic acid or ascorbate to the patient.
2. A method of treating a patient with L-ascorbic acid or ascorbate, wherein the patient is concomitantly treated with at least one statin.
3. A method of concomitantly administering at least one statin and L-ascorbic acid or ascorbate to a patient for treating or preventing cardiovascular disease.
4. The method of using L-ascorbic acid or ascorbate for mitigating the vascular calcification induced by statins.
5. A pharmaceutical composition containing at least one statin and L-ascorbic acid or ascorbate in a dosage form that allows for the concomitant administering of the at least one statin and L-ascorbic acid or ascorbate to a patient.
6. The pharmaceutical composition according to embodiment 5, wherein the at least one statin and L-ascorbic acid or ascorbate are present as a physical mixture or as separate pharmaceutical compositions intended for concomitant administration to a patient.
7. The pharmaceutical composition according to embodiment 5 for the prevention or treatment of cardiovascular disease.
8. The pharmaceutical composition according to one of embodiments 5 to 7, wherein the cardiovascular disease is coronary artery disease, cerebrovascular disease or peripheral vascular disease.
9. The pharmaceutical composition according to one of embodiments 5 to 8, wherein the statin is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin.
10. The pharmaceutical composition according to one of embodiments 5 to 9, wherein the ascorbate is selected from water-soluble or lipid-soluble ascorbates, or mixtures thereof, preferably from calcium ascorbate, magnesium ascorbate, sodium ascorbate, ascorbyl phosphate, ascorbyl palmitate or mixtures thereof.
11. The pharmaceutical composition according to one of embodiments 5 to 10, additionally containing coenzyme Q10 in a dosage form that allows for the concomitant administering of the at least one statin, L-ascorbic acid or ascorbate, and coenzyme Q10 to a patient.
12. The pharmaceutical composition according to one of embodiments 5 to 11, comprising a daily dosage amount of L-ascorbic acid or ascorbate from 10 mg to 100 g, preferably 100 mg to 10 g, and the lowest to the highest commercially available or clinically applicable dose of the at least one statin, preferably from 5 mg to 100 mg.
13. The pharmaceutical composition according to one of embodiments 5 to 12, further comprising one or more additional micronutrients beside L-ascorbic acid or ascorbate.
14. The pharmaceutical composition according to embodiment 13, wherein the one or more additional micronutrients are selected from trace minerals, vitamins, and mixtures thereof, and preferably contain niacin, which can be present in a mixture with the statin.
15. A method for counteracting statin-associated elevated vascular calcification in a subject in need of such treatment which comprises the concomitant administration of an effective amount of at least one statin and an effective amount of L-ascorbic acid or ascorbate.
16. A method for treating or preventing vascular calcification in a patient which comprises the administration of an effective amount of L-ascorbic acid or ascorbate to the patient.

DETAILED DESCRIPTION

According to the present invention, it has been found that L-ascorbic acid or ascorbate is effective in treating or preventing the vascular calcification in a human system, especially when co-administered with statin.

Vitamin C is an essential nutrient for certain animals including humans. Clinical trials have shown a significant positive effect of vitamin C on endothelial function when taken at doses greater than 500 mg per day. Its possible influence on the treatment or prevention of cardiovascular disease has been discussed.

Vitamin C is a very powerful antioxidant and is essential for the formation of collagen and optimum extracellular matrix (ECM). It can prevent lipoprotein deposition and development of atherosclerosis by protecting the integrity and strength of the vascular wall.

Our previous studies have shown that ascorbate can inhibit excessive proliferation and migration of SMC in vitro (Ivanov V, Ivanova S, Roomi M W, Kalinovsky T, Niedzwiecki A, Rath M. Extracellular matrix-mediated control of aortic smooth muscle cell growth and migration by a combination of ascorbic acid, lysine, proline, and catechins. J Cardiovasc Pharmacol 2007; 50:541-547). Also, dietary vitamin C is essential in prevention of lipoproteins deposition in the vascular wall and atherosclerosis in genetically engineered mice mimicking human metabolism in respect their inability to produce vitamin C and expressing human lipoprotein (a) (Cha J, Niedzwiecki A, Rath M. Hypoascorbemia induces atherosclerosis and vascular deposition of lipoprotein(a) in transgenic mice. Am J Cardiovasc Dis 2015; 5:53-62). In a clinical study, a daily micronutrient supplementation, including about 4 grams of vitamin C, was able to halt the progression of coronary calcifications in patients diagnosed with early coronary artery disease (Rath M, Niedzwiecki A. (1996) Nutritional supplement program halts progression of early coronary atherosclerosis documented by ultrafast computed tomography. J Appl Nutr 1996; 48:67-78).

Thus, it is conceivable that vitamin C plays a decisive role in regulating the cellular and extracellular architecture and function inside the vascular wall. With optimum availability of ascorbate, the integrity and stability of the vascular wall would be provided, above all, by an optimum synthesis of collagen and other ECM molecules. In chronic ascorbate deficiency or beginning scurvy, the need for compensatory mechanisms may arise to add compensatory stability to a structurally impaired vascular wall—including by means of calcification.

We investigated the effects of vitamin C on vascular SMC, human dermal fibroblasts (DF) as well as on immortalized human fetal osteoblasts (FOB) and the potential of these cells to contribute to vascular calcification. Moreover, we evaluated the role of statins in connection with this regulatory process, in light of the fact that these drugs are currently taken by millions of patients in the expectation that they curb vascular calcification. Thereby, we came to the invention as disclosed herewith.

According to the present invention, vitamin C, also known as ascorbic acid or L-ascorbic acid, is employed. As an alternative, ascorbate can be employed, wherein the ascorbate, a salt of ascorbic acid with bases or acids stronger than ascorbic acid, is preferably selected from water-soluble or lipid-soluble ascorbates or mixtures thereof and is more preferably selected from the group consisting of calcium ascorbate, magnesium ascorbate, sodium ascorbate, ascorbyl phosphate, ascorbyl palmitate or mixtures thereof.

The L-ascorbic acid or ascorbate is (preferably) administered to patients that are treated with statins.

In the context of the present invention, statins can also be described as HMG-CoA reductase inhibitors. Thus, the statins inhibit the enzyme HMG-CoA reductase which is necessary to make cholesterol. Thus, statins relate to a class of lipid-lowering medications that reduce illness and mortality in those who are at high risk of cardiovascular disease. All suitable statins can be employed in the context of the present invention. Preferably, the stain is selected from the group consisting of atorvastatin, cerivastatin, fluvastatin, lovastatin, mevastatin, pitavastatin, pravastatin, rosuvastatin, simvastatin, or mixtures thereof, or any other type or form of statin, or from a combination of the statin with niacin.

According to one aspect of the invention, the L-ascorbic acid or ascorbate and statin can be administered together with one or more additional micronutrients beside L-ascorbic acid or ascorbate. For example, a pharmaceutical composition comprising statin, L-ascorbic acid or ascorbate, and one or more additional micronutrients can be provided for this purpose.

Preferably, the one or more additional micronutrients are administered together with L-ascorbic acid or ascorbate and with statin. The one or more micronutrients are preferably selected from trace minerals, vitamins different from ascorbate/vitamin C, and mixtures thereof. Trace minerals are only required in small amounts (traces) by humans.

Trace minerals are preferably selected from boron, cobalt (preferably as a component of vitamin B12), chromium, copper, iodine, iron, manganese, molybdenum, selenium, zinc, and mixtures thereof.

Vitamins different from vitamin C are preferably selected from vitamin B complex, vitamin B1 (thiamin), vitamin B2 (riboflavin), vitamin B3 (niacin), vitamin B5 (pantothenic acid), vitamin B6 group including pyridoxine, pyridoxal-5-phosphate, and pyridoxamine, vitamin B7 (biotin), vitamin B9 (folate), vitamin B12 (cobalamin), choline, vitamin A (e.g. retinol or provitamin A carotenoids), vitamin D, including ergocalciferol and cholecalciferol, vitamin E (tocopherols and tocotrienols), vitamin K including vitamin K1 (phylloquinone) and vitamin K2 (menaquinone), carotenoids, including alpha carotene, beta carotene, cryptoxanthin, lutein, lycopene and Zeaxanthin.

When a patient is treated with statins, the daily dosage amount can be from the lowest to the highest commercially available or clinically applicable dose. The dosage amount is preferably in the range of from 5 to 100 mg, preferred 10 to 80 mg, more preferably 10 to 40 mg, most preferably 10 to 20 mg.

The amount of L-ascorbic acid or ascorbate administered to a patient receiving statin treatment is preferably 10 mg to 100 g, more preferably 100 mg to 10 g, most preferably 200 mg to 5 g daily dosage.

It is possible to administer the L-ascorbic acid or ascorbate (and optional one or more additional micronutrients) simultaneously with the statin, for example in a tablet containing both, L-ascorbic acid or ascorbate (and optional one or more additional micronutrients), and statin. Furthermore, it is possible to administer L-ascorbic acid or ascorbate (and optional one or more additional micronutrients) and statin in separate pharmaceutical compositions, but concomitantly. The term "concomitantly" means that the administration of both active ingredients takes place within a time range of from 0 to 5 hours, preferably 0 to 3 hours, more preferably 0 to 1 hours, based on one administration per day.

Since both statins and L-ascorbic acid or ascorbate (as well as other/additional micronutrients different from vitamin C) are well established for an individual and separate administration to patients in need thereof, the known pharmaceutical or nutritional compositions can be employed according to the present invention while ensuring the concomitant use of both active ingredients.

If necessary, one or both of the ingredients can be combined with coenzyme $Q_{10}$ in a combined pharmaceutical composition or in separate pharmaceutical compositions, as outlined in U.S. Pat. No. 4,929,437.

According to the present invention, L-ascorbic acid or ascorbate is used for treating or preventing the vascular calcification, specifically the vascular calcification induced in patients by administration of statins.

The term "treating" in this context means "mitigating" or "reversing".

Specifically, the calcification of vascular smooth muscle cells (SMC), more specifically human aortic smooth muscle cells (AoSMC) shall be prevented or mitigated. The present invention is specifically based on the positive effect of vitamin C on vascular SMC, human dermal fibroblasts (DF) as well as immortalized human fetal osteoblasts (FOB). The process of vascular calcification requires a phenotypic transformation of vascular smooth muscle cells (VSMC) into osteogenic cells.

The concomitant administration of at least one statin and L-ascorbic acid or ascorbate to a patient is helpful for treating or preventing cardiovascular disease, for example coronary artery disease, cerebrovascular disease or peripheral vascular disease.

By applying the present invention, the increased calcification observed under long-term statin treatments can be mitigated, reversed or prevented. Thus, there is no need for a hypothetical interpretation that the statin-induced calcification could be beneficial or that there could be a beneficial macro-calcification, as opposed to detrimental micro-calcification.

Materials and Methods
Reagents

All reagents were from Sigma-Aldrich (St. Louis, Mo., USA) except when indicated differently.

Cell Cultures

Normal human dermal fibroblasts (DF) and immortalized human fetal osteoblasts (hFOB) were supplied by ATCC (Manassas, Va., USA). Human aortic smooth muscle cells (AoSMC) were purchased from Cambrix (East Rutherford, N.J.) and used in experiments at 5-7 passages. Cell cultures were maintained in DMEM medium (ATCC) containing antibiotics and 5% fetal bovine serum (FBS, ATCC). In some experiments cells were incubated in pro-osteogenic medium, defines as 5% FBS/DMEM fortified with 5 mM beta-glycerophosphate with or without 25 mcM forskolin. All cell cultures were maintained at 37° C. and 5% $CO_2$ atmosphere. Cell viability was monitored with MTT assay.

Alkaline Phosphatase Activity Assay in AoSMC

AoSMC were plated in 96 well plates and grown to confluent layer. Cells were incubated with ascorbic acid in growth medium for three days. Cells were washed with phosphate buffered saline (PBS) and supplemented with 50 mcl/well 25 mcg/ml 4-MUP (fluorescent ALP substrate, Sigma) in alkaline buffer (Sigma)/1% Triton X100 for 1 h at room temperature. Fluorescence was measured at 360/450 nm.

Calcium Accumulation in Extracellular Matrix

AoSMC were seeded on fibronectin covered plastic plates at density 25,000 per square cm and grown to confluence for 5-7 days. Ascorbic acid was added to cells at indicated concentrations for 72 hours in DMEM supplemented with 2% FBS and cell-produced extracellular matrix was exposed by sequential treatment with 0.5% Triton X100 and 20 mM ammonium sulfate in phosphate buffered saline (PBS, Life Technologies) for 3 min each at room temperature as described in Ivanov V, Ivanova S, Kalinovsky T, Niedzwiecki A, Rath M. Plant-derived micronutrients suppress monocyte adhesion to cultured human aortic endothelial cell layer by modulating its extracellular matrix composition. J Cardiovasc Pharmacol 2008; 52:55-65. After four washes with PBS, ECM layers were solubilized by incubation in 0.6N HCl for 48 hours at 37° C. Calcium content in solubilized samples was measured with TECO Ca assay according to manufacturer's protocol.

Expression of Osteoblasts Markers in Human Cultured Cells

For the experiments AoSMC, DF and hFOB cells were seeded in separate 96 well plastic plates at density 25,000 per square cm and grown to confluence for 5-7 days. Tested compounds were added to cells at indicated concentrations for 72 hours in DMEM supplemented with 2% FBS. Cell layers were washed three times with PBS and fixed with 3% formaldehyde in PBS at 4° C. for one hour. Fixed cell layers were washed four times with PBS and treated with 1% BSA/PBS for one hour at RT. Immunoassay for osteogenic markers was done by sequential incubation with primary monoclonal antibodies (R&D Systems) in 1% BSA/PBS for 2 hours followed by 1 hour incubation with secondary goat anti-mouse IgG antibodies labeled with horse radish peroxidase (HRP). Retained peroxidase activity was measured after the last washing cycle (three times with 0.1% BSA/PBS) using TMB peroxidase substrate reagent (Rockland). Optical density was read with plate reader (Molecular Devices) at 450 nm and expressed as percentage of control cell samples incubated in unsupplemented 2% FBS/DMEM. To ensure a direct comparison of osteogenic markers expression on different cell types all pcell covered plates were treated identical and simultaneously during immunoassay.

Statistical Analysis

Results in figures are means±standard deviation (SD) from three or more repetitions from the most representative of at least two independent experiments. Differences between samples were estimated with a two-tailed Student's t-test using Excel software (Microsoft) and accepted as significant at p levels less than 0.05.

Results

Figure 1:
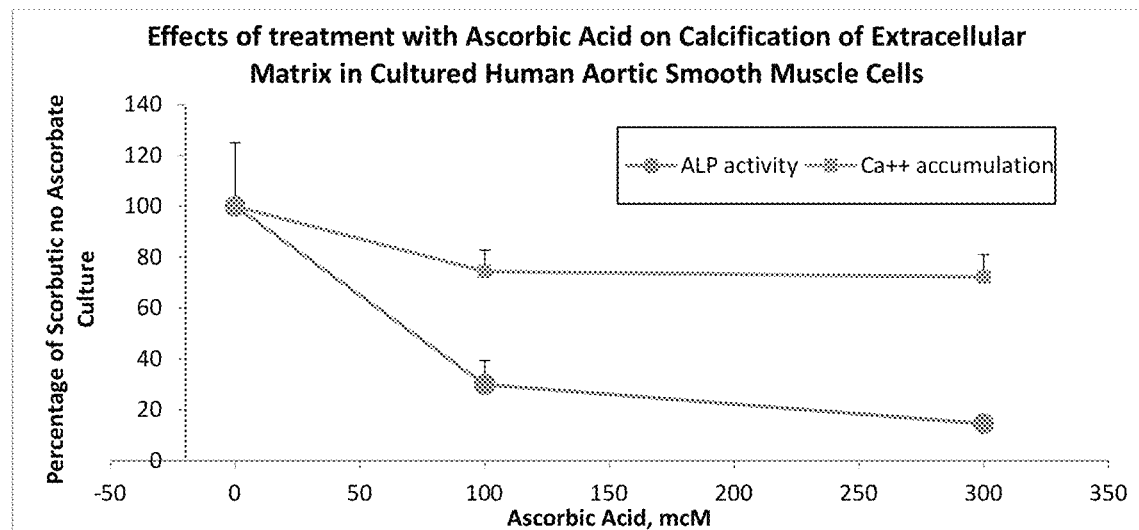
FIG. 1 shows the effects of treatment with ascorbic acid on calcification of extracellular matrix in cultured human aortic smooth muscle cells.

Cellular calcification process was investigated in human AoSMC cultured in a regular cell growth medium (5% FBS/DMEM) in the absence and presence of various amounts of ascorbic acid. The calcification process of AoSMC was evaluated by the activity of cellular alkaline phosphatase and calcium accumulation in the cell-produced extracellular matrix (FIG. 1).

The results show that supplementation of AoSMC medium with ascorbic acid up to 300 mcM resulted in a significant decrease in the level of extracellular calcium and lower activity of cellular alkaline phosphatase in dose-dependent manner. In the presence of 300 mcM ascorbate the extracellular Ca accumulation by AoSMC decreased by 20% and alkaline phosphatase activity by 80%.

Figure 2A:
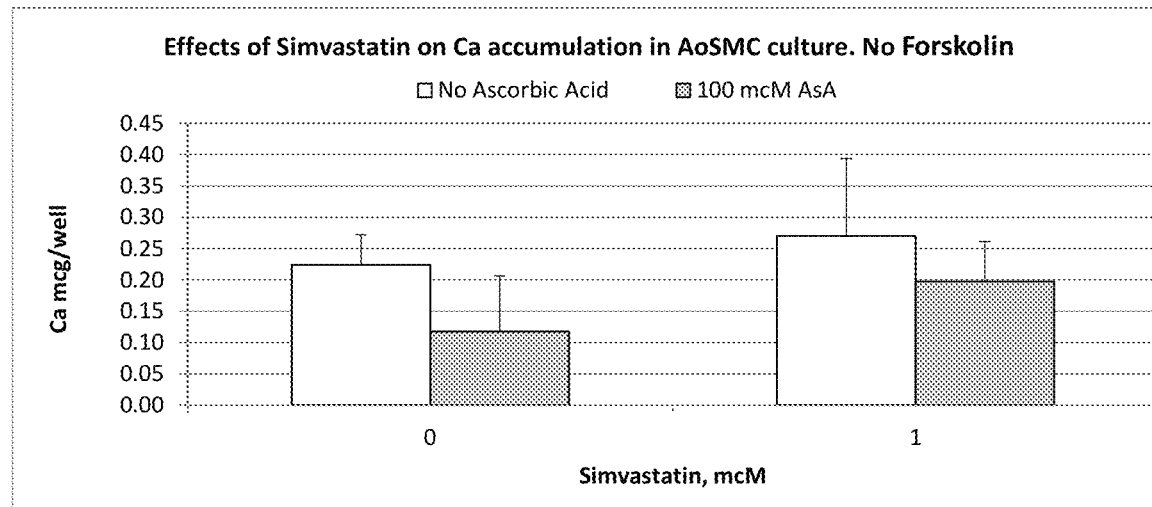
FIG. 2A shows the effects of Simvastatin on Ca accumulation in AoSMC culture without forskolin.

The results presented in FIG. 2A show that calcium accumulation in AoSMC layers was increased in the presence of simvastatin by 23%. However, concomitant presence of 100 mcM ascorbate calcium resulted in a 54% decrease of accumulated calcium to the value 0.2 mcg/well, which correlated with the values observed in cells not exposed to simvastatin.

Figure 2B:
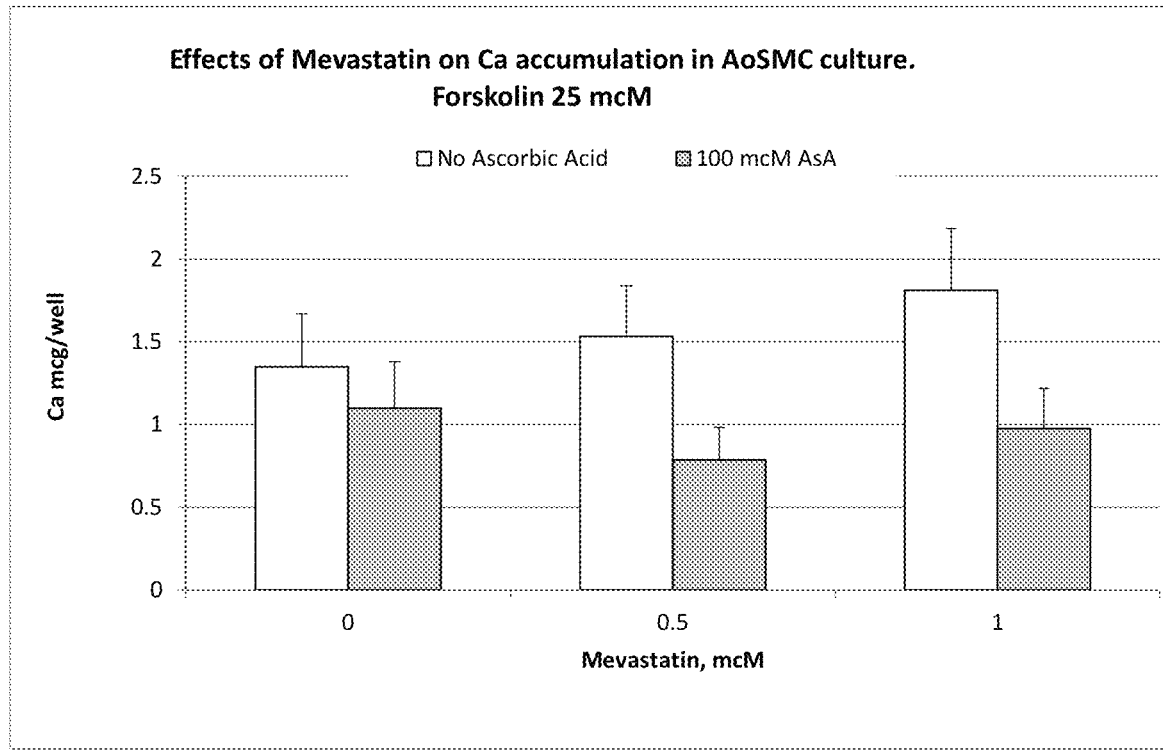
FIG. 2B shows the effects of mevastatin on Ca accumulation in AoSMC culture with 25 mcM forskolin.

The effect of ascorbate on calcium accumulation in AoSMC under enhanced pro-calcification condition (with forskolin) and in the presence of a statin (mevastatin) is presented in FIG. 2B. The results show that in the presence of 1 mM mevastatin calcium accumulation increased from 1.35 mcg/well in control to 1.8 mcg/well with mevastatin. However, when 100 mcM ascorbate was added calcium accumulation decreased by 19% to below control (non-supplemented) values.

Figure 3A:
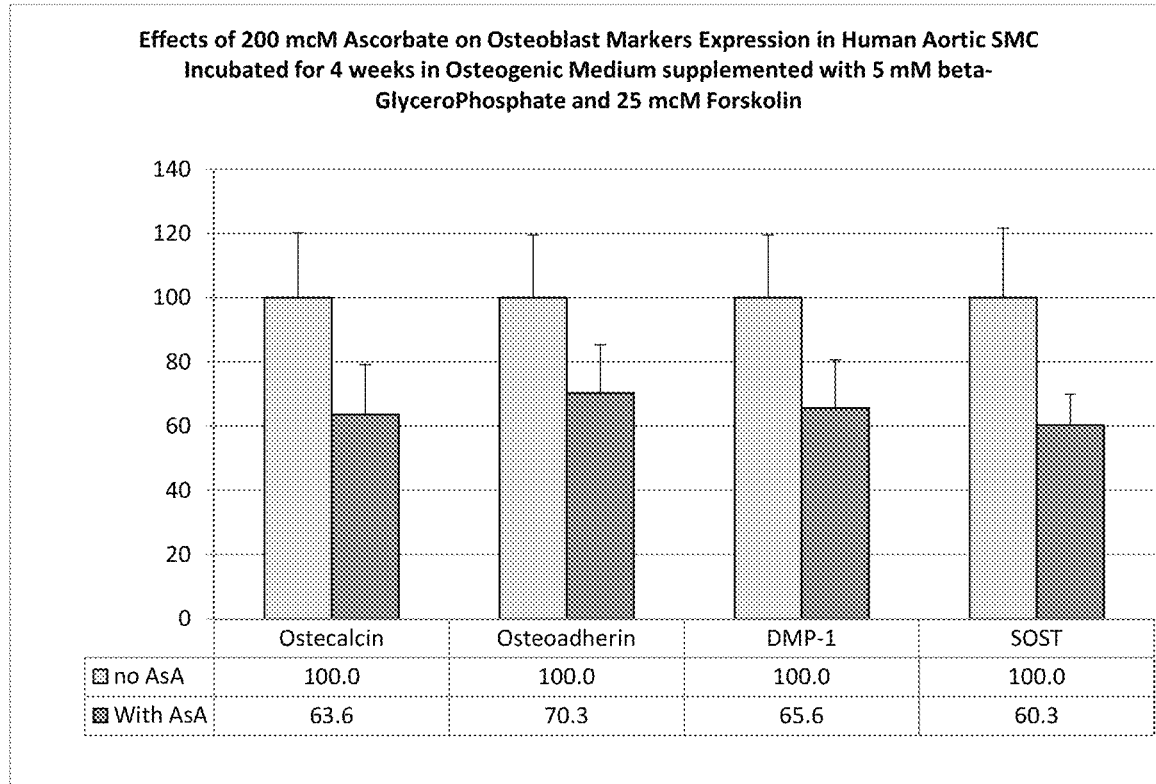
FIG. 3A shows the effects of 200 mcM ascorbate on osteoblast markers expression in human aortic SMC incubated for 4 weeks in osteogenic medium supplemented with 5 mM beta-glycerophosphate and 25 mcM forskolin.
Figure 3B:
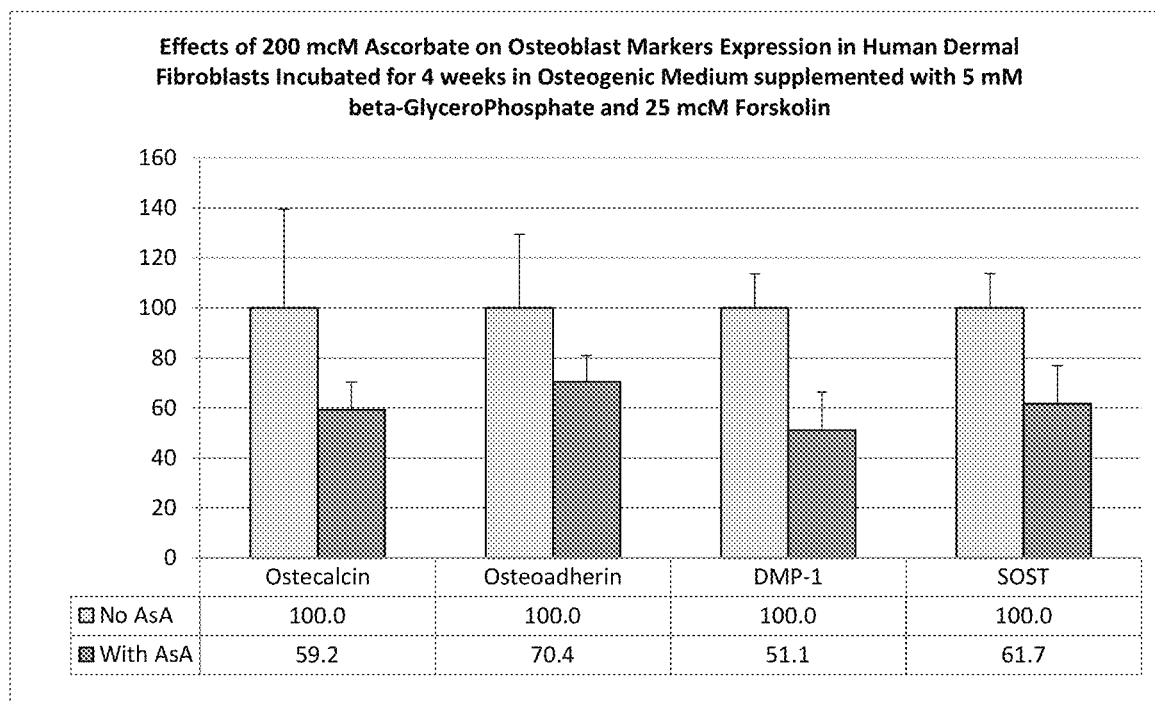
FIG. 3B shows effects of 200 mcM ascorbate on osteoblast markers expression in human dermal fibroblasts incubated for 4 weeks in osteogenic medium supplemented with 5 mM beta-glycerophosphate and 25 mcM forskolin.

In addition to SMC we studied the effect of ascorbate on cellular calcification process in human dermal fibroblasts (DF) and immortalized human fetal osteoblasts (FOB) by evaluating changes in the expression of different pro-osteogenic markers in these cells. The effects of ascorbate in different types of cells challenged with pro-osteogenic conditions such as by growing them in the medium supplemented with 5 mM beta-glycerophosphate and 25 mcM forskolin. The results show that expression of all tested osteogenic markers was significantly reduced by 100 mcM ascorbic acid supplementation in both AoSMC and DF cultures (FIG. 3). Ascorbic acid supplementation of hFOS osteoblasts in pro-osteogenic medium over four week period was cytotoxic. Corresponding data were omitted from the presentation.

We compared the levels of osteogenic markers expression in the test human cell types as presented in Table 1. The results indicate that in a regular growth medium, the expression of osteocalcin, osteoadherin, dentin matrix protein 1 (DMP-1) and sclerostin (SOST) were most prominent in osteoblasts cells (FOB) closely followed by fibroblasts (DF), except of DMP-1, expression of which in fibroblasts slightly overcame that of FOB cultures. Cellular expression of these four osteogenic markers in AoSMC cultured in regular growth medium was significantly (2-4) fold less prominent than in FOB and DF cultures.

In the present tests we demonstrated that ascorbic acid tested up to 300 mcM concentrations can reduce calcium accumulation in ECM produced by AoSMC. This effect was accompanied by the blockage of SMC osteogenic transformation as indicated by changes in specific metabolic parameters, such as reduction in cellular alkaline phosphatase activity, and cellular expression of osteoblast marker proteins. A high level of serum alkaline phosphatase (ALP) is associated with an increased risk of mortality and myocardial infarction. ALP hydrolyses inorganic pyrophosphate, which is a strong inhibitor of calcium phosphate deposition.

Under physiological conditions (cells incubated in regular cell culture medium) expression of osteocalcin, osteoadherin and SOST/sclerostin were the highest in hFOS cultures and the lowest in hAoSMC cultures. Expression of these markers were intermediate in hDF cultures. Under physiological conditions (cells incubated in regular cell culture medium) expression of DMP-1 was the highest in hDF cultures and the lowest in hAoSMC cultures. Expression of DMP-1 was intermediate in hFOS cultures. Cell supplementation with pro-osteogenic medium as compared to regular medium caused stimulation of all tested osteomarkers in AoSMC cultures. In contrast, pro-osteogenic medium supplementation caused an inhibition of all tested osteogenic markers in hDF and hFOS cultures.

The claimed invention is:

1. A daily dosage form consisting of a pharmaceutical composition consisting of at least one statin, L-ascorbic acid or ascorbate, vitamin B12, vitamin B5, vitamin B1, vitamin B2, vitamin B6, vitamin B7, vitamin B9, vitamin E, and optionally niacin and/or coenzyme Q10, wherein the amount of the L-ascorbic acid or ascorbate is from 100 mg to 10 g and the amount of the at least one statin is from 5 mg to 100 mg.

2. The daily dosage form according to claim 1 for the prevention or treatment of cardiovascular disease.

3. The daily dosage form according to claim 2, wherein the cardiovascular disease is coronary artery disease, cerebrovascular disease or peripheral vascular disease.

4. The daily dosage form according to claim 1, wherein the statin is selected from the group consisting of atorvastatin, cerivastatin, fluvastatin, lovastatin, mevastatin, pitavastatin, pravastatin, rosuvastatin, simvastatin, or mixtures thereof.

5. The daily dosage form according to claim 1, wherein the niacin is present.

6. The daily dosage form according to claim 1, wherein the ascorbate is selected from water soluble or lipid soluble ascorbates, or mixtures thereof.

7. The daily dosage form according to claim 6, wherein the ascorbate is selected from calcium ascorbate, magnesium ascorbate, sodium ascorbate, ascorbyl phosphate, ascorbyl palmitate or mixtures thereof.

8. The daily dosage form according to claim 1, wherein the coenzyme Q10 is present.

TABLE 1

| Cell type | | Osteogenic Marker | | | | | | | |
|---|---|---|---|---|---|---|---|---|---|
| | | Osteocalcin mean | sd | Osteoadherin/ OSAD mean | sd | DMP-1 mean | sd | SOST/ Sclerostin mean | sd |
| AoSMC | Plain Medium | 0.288 | 0.047 | 0.259 | 0.025 | 0.412 | 0.063 | 0.212 | 0.030 |
| | Osteogenic Medium | 0.429 | 0.086 | 0.315 | 0.061 | 0.569 | 0.111 | 0.289 | 0.063 |
| hDF | Plain Medium | 1.087 | 0.051 | 0.889 | 0.093 | 1.137 | 0.089 | 0.657 | 0.058 |
| | Osteogenic Medium | 0.614 | 0.242 | 0.403 | 0.119 | 0.851 | 0.116 | 0.374 | 0.051 |
| FOS | Plain Medium | 1.206 | 0.288 | 1.493 | 0.147 | 0.819 | 0.307 | 0.956 | 0.197 |
| | Osteogenic Medium | 1.003 | 0.207 | 1.049 | 0.213 | 0.786 | 0.078 | 0.633 | 0.126 |

9. The daily dosage form according to claim 1, comprising a daily dosage amount of the L-ascorbic acid or ascorbate from 200 mg to 5 g, and of the at least one statin from 10 mg to 80 mg.

10. The daily dosage form according to claim 1, wherein the daily dosage form is for the prevention or treatment of vascular calcifications.

11. The daily dosage form according to claim 10, wherein the vascular calcifications are coronary vascular calcification, cerebrovascular calcification, or peripheral vascular calcification.

12. The daily dosage form according to claim 1, comprising a daily dosage amount of the at least one statin from 10 mg to 40 mg.

13. The daily dosage form according to claim 1, comprising a daily dosage amount of the at least one statin from 10 mg to 20 mg.

\* \* \* \* \*